(12) United States Patent
Calkin

(10) Patent No.: US 7,712,645 B2
(45) Date of Patent: May 11, 2010

(54) MEDICAL CHEST BAG FOR MILITARY, EMERGENCY RESCUE AND OTHER PERSONNEL

(76) Inventor: Carston R. Calkin, P.O. Box 3390, Tualatin, OR (US) 97062

( * ) Notice: Subject to any disclaimer, the term of this patent is extended or adjusted under 35 U.S.C. 154(b) by 245 days.

(21) Appl. No.: 11/732,532

(22) Filed: Apr. 3, 2007

(65) Prior Publication Data
US 2008/0121730 A1    May 29, 2008

Related U.S. Application Data

(60) Provisional application No. 60/793,542, filed on Apr. 19, 2006.

(51) Int. Cl.
*A45F 3/04* (2006.01)
*A45F 3/06* (2006.01)

(52) U.S. Cl. .................. 224/649; 224/191; 224/235; 224/930

(58) Field of Classification Search ............... 224/153, 224/155, 196, 235, 270, 575–581, 649, 914, 224/930

See application file for complete search history.

(56) References Cited

U.S. PATENT DOCUMENTS

| 2,324,194 | A | * | 7/1943 | Campiglia | ............ 224/623 |
| 4,171,760 | A | * | 10/1979 | Gay | ............ 224/241 |
| 5,503,316 | A | * | 4/1996 | Stewart | ............ 224/312 |
| 5,586,703 | A | * | 12/1996 | Radar et al. | ............ 224/601 |
| 5,632,428 | A | * | 5/1997 | Weiss | ............ 224/623 |
| 6,161,738 | A | * | 12/2000 | Norris | ............ 224/153 |
| 6,216,926 | B1 | * | 4/2001 | Pratt | ............ 224/153 |
| 6,382,490 | B1 | * | 5/2002 | Divincenzo | ............ 224/681 |
| 7,458,491 | B2 | | 12/2008 | Cragg | |
| 2004/0011841 | A1 | * | 1/2004 | Sprague et al. | ............ 224/638 |
| 2004/0245304 | A1 | | 12/2004 | Cragg | |
| 2008/0257929 | A1 | | 10/2008 | Cragg | |

* cited by examiner

*Primary Examiner*—Nathan J Newhouse
*Assistant Examiner*—Adam Waggenspack
(74) *Attorney, Agent, or Firm*—Stoel Rives LLP (57) ABSTRACT

A chest bag apparatus is arranged to be worn and carried in position secured against the chest of a wearer both in a first, closed, carrying condition and in a second, open, substantially L-shaped, tray-like condition providing facilitated access to the interior of the bag and its contents during its use while being worn by a wearer. The chest bag may further have a second, fully open condition for use of the chest bag in a hanging condition on a support hook or in condition laid out on an underlying ground surface. The chest bag preferably includes a quick release, temporary closure arrangement to permit the bag to be quickly closed temporarily so that it does not obstruct the wearer's view and activity.

23 Claims, 4 Drawing Sheets

MEDICAL CHEST BAG FOR MILITARY, EMERGENCY RESCUE AND OTHER PERSONNEL

This application claims benefit under 35 U.S.C. 119(e) of the priority filing of U.S. Provisional application Ser. No. 60/193,542, filed 19 Apr. 2006.

BACKGROUND OF THE INVENTION

This invention relates to utility bags arranged to be secured to and carried on the body of the wearer, such as backpacks and the like, and more particularly to a utility bag arranged to be worn, carried and accessed while worn in a supported condition against the chest area of a wearer.

Utility bags that are arranged to be secured onto and worn on the body of a person are known and have come in various forms arranged for the particular contents to be carried and the need of the wearer. Examples of such bags are backpacks, Fanny packs and small packs arranged to be worn in front at the waist, for convenient access to the contents of the pack as it is being worn. Many other types of bags and packs have been provided for support on a carrying strap slung over the shoulder of a wearer, such as purses, etc. However, these bag structures are not primarily arranged or configured to permit convenient access to their interior while the bag is being worn.

In military and emergency rescue situations however, personnel invariably have to carry, either on their person or in their hands, a great deal of burdensome equipment and supplies related to their specialties when they are in the field. An example is combat lifesavers, corpsmen and medics in military situations when in addition to the gear that they carry as soldiers in the field, they also need to carry supplies of first aid materials, bandages, splints, I.V. bags, medications and a multitude of other very important supplies and equipment necessary for rendering emergency aid to a soldier or civilian injured in the field and in urgent need of immediate treatment before being transported to a safer area or a medical aid station for comprehensive care. Of course, it is preferable that various supplies be held within the dedicated bag in an organized manner so that they may be readily accessed when needed in an emergency situation, as well as to facilitate inventory upkeep as those skilled in the art will readily recognize.

SUMMARY OF THE INVENTION

In its basic concept this invention provides a chest bag arranged to be secured by shoulder-encircling straps onto a wearer and worn and carried in a supported position secured in condition against and overlying the chest area of the wearer both in a first, closed, carrying condition and in a second, open, substantially L-shaped, tray-like condition providing facilitated access to the interior of the bag and its contents during its use while worn by the wearer.

It is by virtue of the foregoing basic concept that the principal objective of this invention is achieved; namely, the provision of a chest bag that not only provides for the secure and protected, hands-free carrying of the bag and its contents, but also permits ready access to the contents of the bag and a provides a tray-like work area for the contents while the chest bag remains continuously worn.

Another object and advantage of this invention is the provision of a chest bag apparatus of the class described which is arranged to be quickly and easily disconnected from the wearer in situations requiring its immediate removal.

Another object and advantage of this invention is the provision of a chest bag apparatus of the class described which may additionally include a waist-encircling strap member arranged to releasably secure the bottom portion of the bag in stable condition snugly against the wearer's torso and against shifting and displacement from the wearer's chest area during the wearer's activities.

Another object and advantage of this invention is the provision of a chest bag apparatus of the class described which may be provided with a selected strap attachment system arranged to releasably mount selected, additional and interchangeable pocket members releasably to the exterior surface of the chest bag if desired for increasing the amount of supplies and equipment that can be carried by the chest bag.

Yet another object and advantage of this invention is the provision of a chest bag apparatus of the class described which may be arranged with interior pockets and holders selected and arranged to hold selected supplies and articles in organized, confined manner to facilitate identification and access to the contents of the bag in emergency conditions.

A further object and advantage of this invention is the provision of a chest bag apparatus of the class described which L-shaped open condition of the bag may be released if desired to permit the user to open the bag fully if needed or desired to permit the bag to be laid in a fully open condition flat on a ground surface or alternatively hung in a fully open condition from a hook in a vehicle for ready and convenient access to the contents of the bag.

A still further object and advantage of this invention is the provision of a chest bag apparatus of the class described which may include temporary quick closure means arranged to permit the bag to be quickly secured temporarily in a closed condition while in use so as not to obstruct, hinder or interfere with the view and activities of a medical rescue personnel wearing the chest bag while tending to a patient.

A still further object and advantage of the present invention is the provision of a chest bag apparatus of the class described which is of simplified construction for economical manufacture and reliability of use.

The foregoing objects and advantages of the present invention will appear from the following detailed description, taken in connection with the accompanying drawings of a preferred embodiment.

DETAILED DESCRIPTION OF THE PREFERRED EMBODIMENTS

A medical chest bag apparatus primarily for use by military medical, emergency and rescue personnel is arranged to be worn and carried in a supported position overlying the chest area of the wearer both in a first, closed, carrying condition and in a second, open, substantially L-shaped, tray-like condition providing facilitated access to the interior of the bag and its contents during its use while worn by a person. For purposes of illustration herein, the chest bag of this invention is shown and described herein in the form of a combat medical lifesaver's bag for use by military medical personnel in the field. However, it will be readily apparent to those skilled in the art, that, although the chest bag apparatus of this invention is very advantageously adapted for use as a combat medical bag, its use in other fields is equally advantageous and is limited only by the particular selection of contents and type and configuration of interior and exterior pockets, etc. provided.

Figure 1:
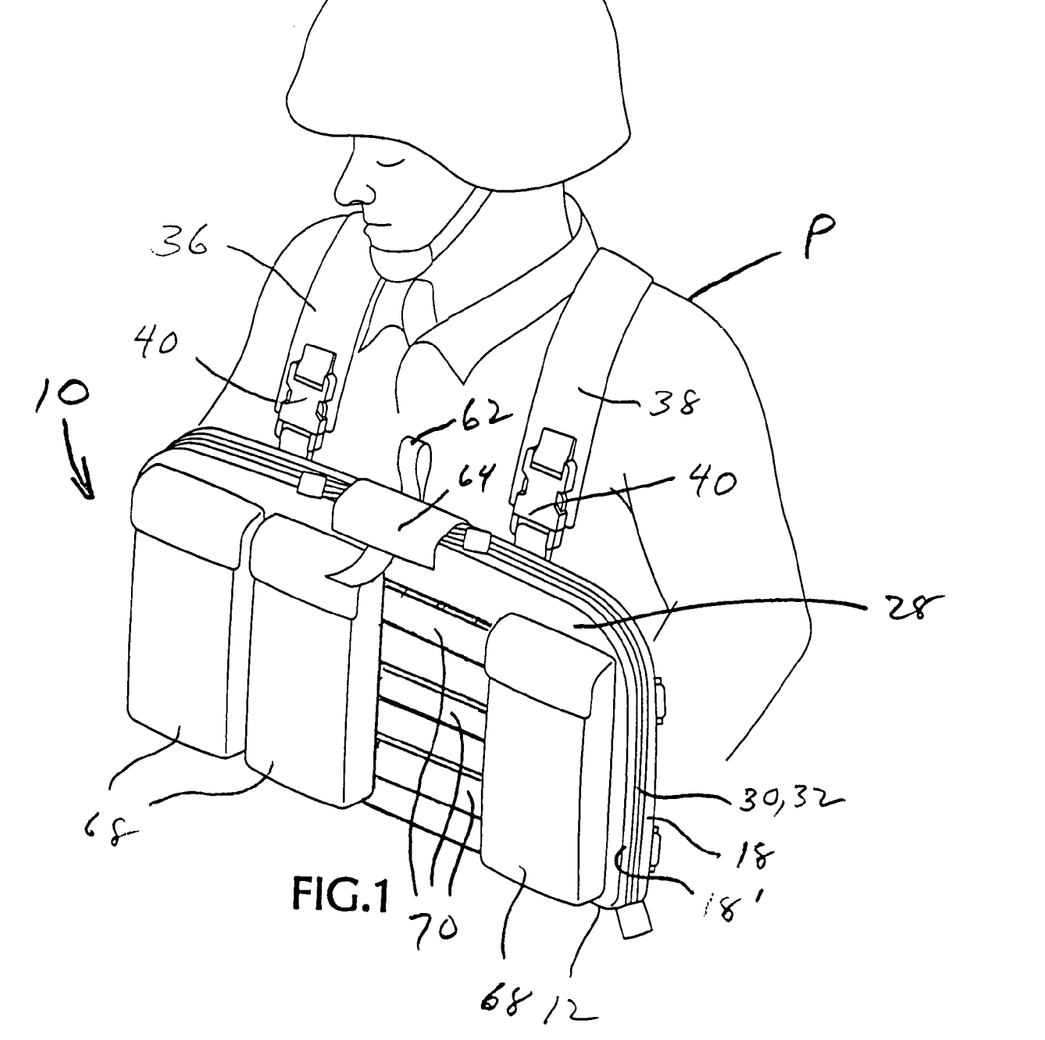
FIG. 1 is a fragmentary, front perspective view of a chest bag embodying features of this invention in closed, transport condition secured onto a wearer in position against the chest of the wearer.

With reference to the drawings, FIG. 1 is a fragmentary front perspective view of a chest bag 10 embodying features of this invention and supported on a wearing personnel P in a first, closed, carried condition positioned over the wearer's chest. In this form of the invention being specifically described herein, the personnel would typically be a medical specialist in a group of combat soldiers, as is well understood in the military.

Figure 2:
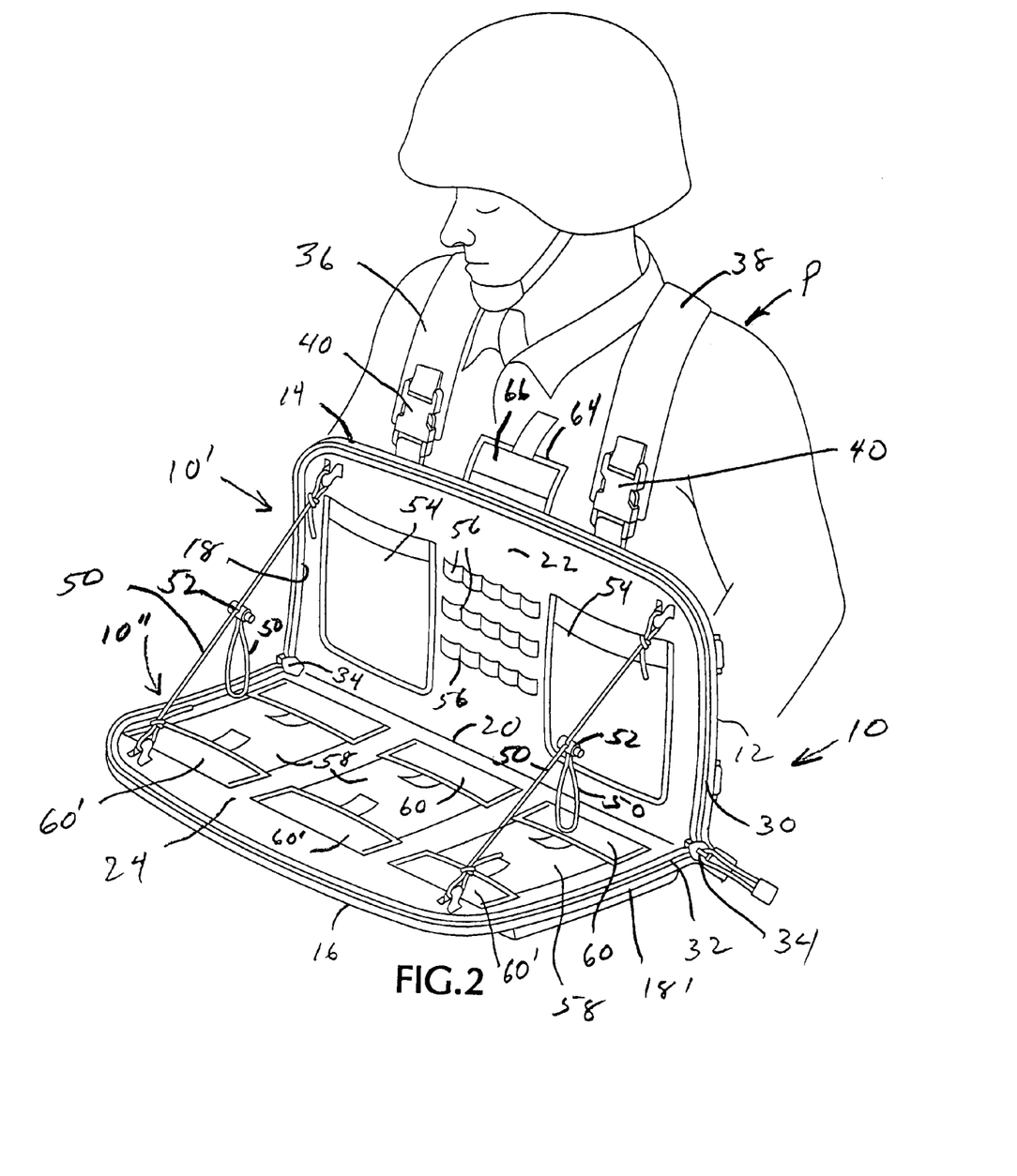
FIG. 2 is a fragmentary, front perspective view of the chest bag of FIG. 1 but in an open, L-shaped, tray-like condition supported on the torso of the wearer for access to the contents contained in the interior of the chest bag while the bag is being worn.
Figure 3:
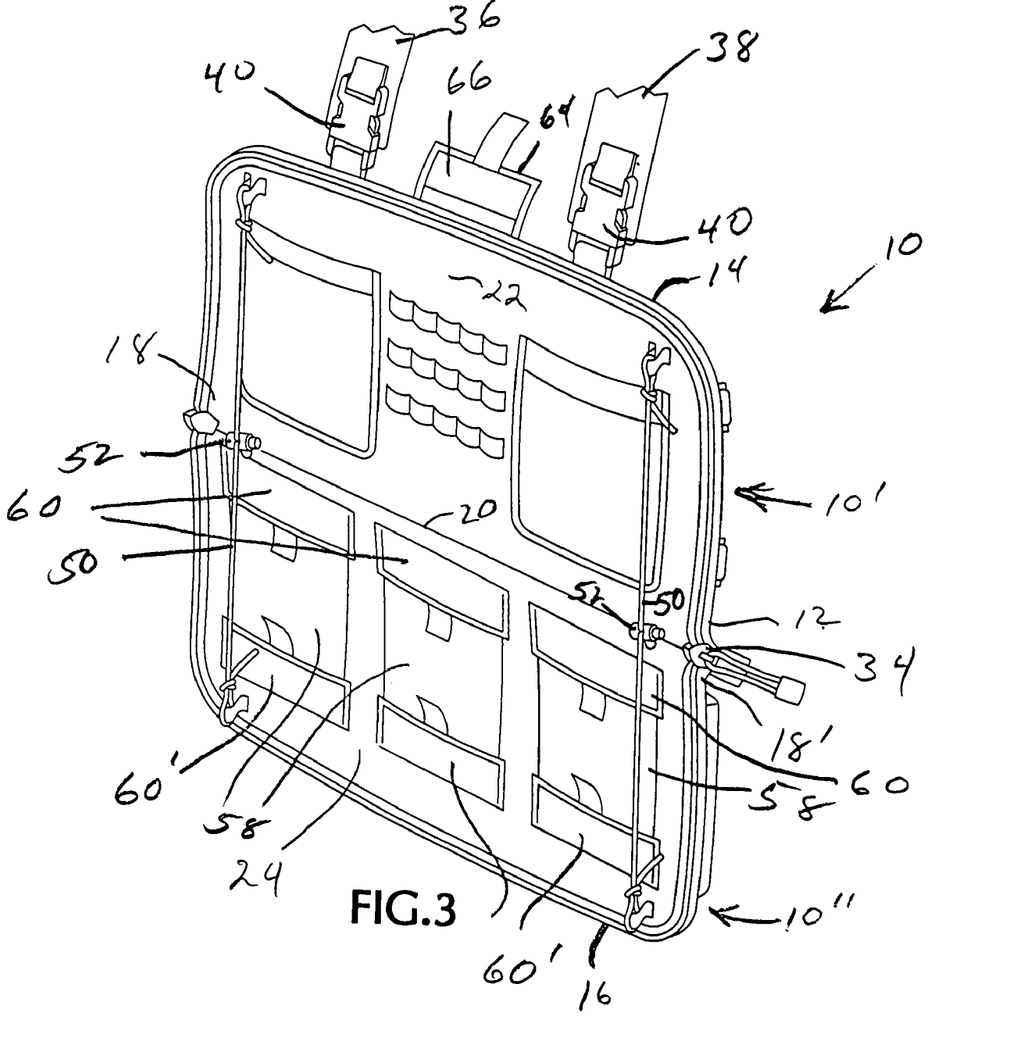
FIG. 3 is a fragmentary, front perspective view of the chest bag in a fully open condition for access to the interior confines of the bag when the bag is supported in hanging condition or condition laid flat on an underlying support surface.

As seen best in FIGS. 1, 2 and 3 of the drawings, the chest bag 10 of this invention comprises a flexible bag body member 12 provided generally in a form somewhat similar to a flexible briefcase-type body, formed in the present embodiment of a selected flexible, fabric sheet material such as canvass, gortex, nylon or other suitable fabric material selected for the purpose.

As is seen in FIGS. 2 and 3, the chest bag body 12, is in the particular embodiment illustrated herein, formed as a generally rectilinear flexible base panel member having a longitudinal dimension defined by longitudinally opposite top and bottom peripheral edges 14, 16 and a lateral, width dimension defined by opposite lateral peripheral side edges 18, 18'. As is shown, the rectilinear base panel member forming the flexible bag member is arranged with a laterally extending fold or hinge line 20 disposed approximately at the longitudinal midpoint of the bag body and extending laterally across its width, thereby effectively dividing the flexible bag body member into opposite sections or halves extending in opposite directions from the fold or hinge line 20. These opposite halves form a first, upper bag section 10', or rear panel member 10', having an interior wall panel 22, and a second, lower bag section 10", or front panel member 10", having an interior wall panel 24. As will be appreciated, the exterior walls of the first and second bag panel members 10', 10" of the flexible bag body form respective exterior rear wall 26 and exterior front wall 28 of the flexible chest bag.

As seen best in FIGS. 1 and 2, the first and second bag sections 10', 10" are arranged to be releasably secured together in the closed condition of FIG. 1. In this regard, the outer peripheral edges of the upper and lower sections extending from the central fold or hinge line 20 mount corresponding interengaging components 30, 32, of a zipper or other slider type fastener apparatus. As is well understood, operation of the slide member 34 of such fasteners in one direction of travel interengages the corresponding zipper or slider components 30, 32 to secure the opposite bag sections 10', 10" in the closed condition of FIG. 1, and operation of the slider member 34 in the opposite direction of travel disengages the interconnected components 30, 32 to release the bag sections for opening of the bag, by pivoting movement of the bag sections on fold or hinge line 20, and access to the inner confines of the bag, as seen in FIGS. 2 and 3.

Figure 4:
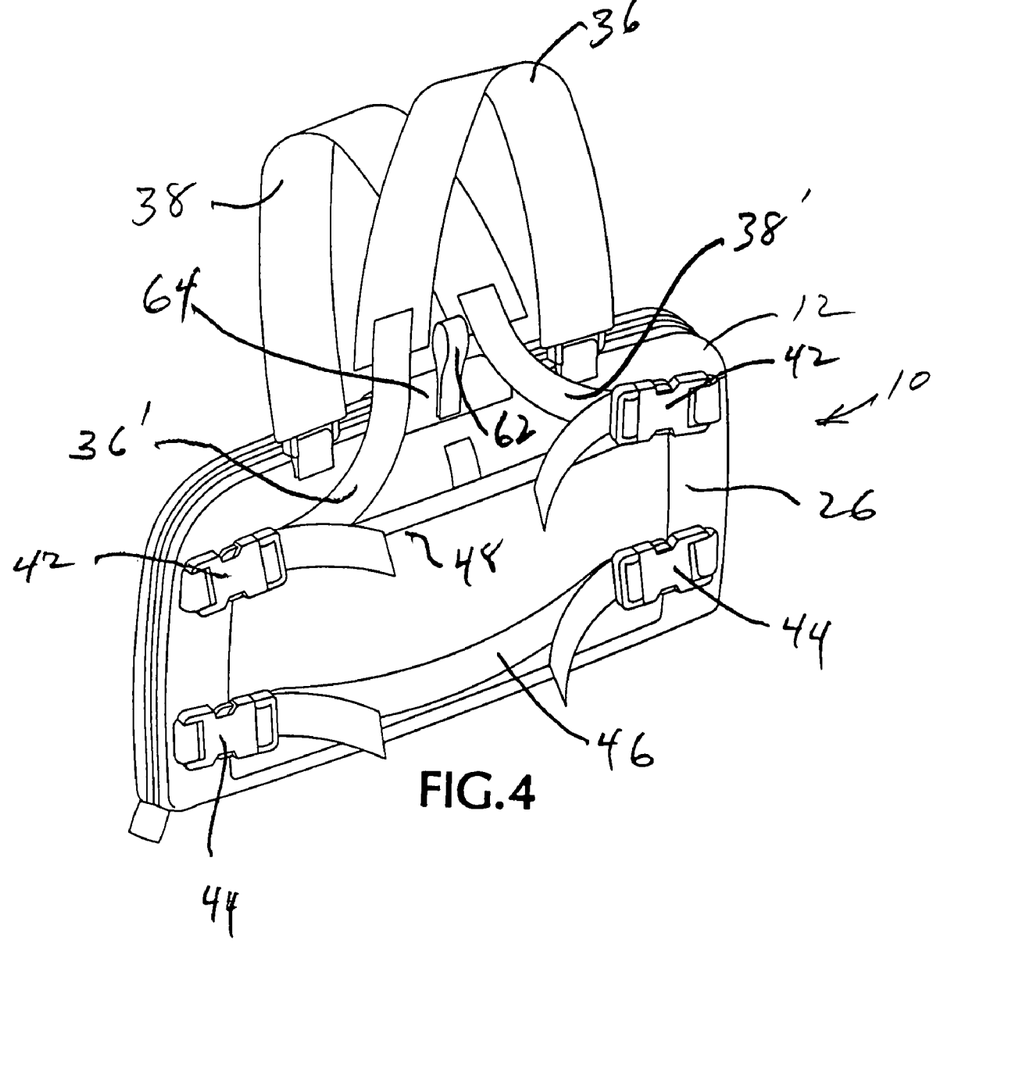
FIG. 4 is a rear perspective view of the chest bag of FIG. 1 showing the back wall of the chest bag and the arrangement of shoulder-encircling and waist-encircling straps preferred for securing the bag onto a wearer.

As seen best in FIGS. 1, 2 and 4 of the drawings, the first, upper section 10' of the medical chest bag of this invention mounts, adjacent its top edge 14, one terminal end of each of a pair of laterally spaced apart, elongated, bag support strap members 36, 38, as by quick release buckle connector apparatus 40. These strap members 36, 38 are arranged to extend upwardly from the bag and over a wearer's shoulders, and downwardly along his back and around the sides of the torso for connection, at their opposite terminal ends, to the rear exterior wall 26 of the upper section 10', as by quick release buckle apparatus 42 shown in FIG. 4.

Preferably, the length of each elongated, shoulder-encircling support strap member 36, 38 between end connections on the bag is arranged for adjustment in order to accommodate desired fit of the supported medical bag on wearers of different sizes, as will be apparent. In the embodiment of FIG. 4, this adjustability feature is provided with strap end sections 36', 38', illustrated herein as lengths of webbing material, adjustably engaging the buckle members 42 in well known arrangement. Preferably, interengaging buckle components of the buckle apparatus 42 are arranged to correspond with respective buckle components typically provided on assault vests, etc. so that if desired, the medical bag of this invention can be attached to such a vest and worn as a butt pack, in known manner well understood in the military.

As is also seen in FIG. 4, the support straps 36, 38 are arranged to preferably cross each other at the wearer's back for extension of the strap members from the bag vertically upward over the shoulder on corresponding right and left sides of the neck for extension of each strap member around the opposite left and right sides, respectively of the torso for connection to the bag at their opposite ends. This crossover support strap arrangement is preferred because, with the medical bag secured snugly against the chest of a wearer as in FIG. 1, the bag is virtually assured against shifting on or other displacement from the wearer during the rigors of his movements.

In the event it is necessary that the wearer hastily remove the medical bag, he need only uncouple the quick release buckle components 40 and the bag will fall away. Also, if needed or desired, the rear panel 26 of the first, upper bag section may releasably mount, as by quick-release buckle apparatus 44, an additional, waist-encircling strap member 46 positioned on the lower portion of the rear exterior wall of upper bag section adjacent the area of the fold hinge line of the bag to secure and retain the lower portion of the bag positively against the wearer's torso.

As is also shown in FIG. 4, in its preferred form the medical chest bag of this invention also preferably provides on the rear exterior wall 26, a long pocket member 48 arranged to hold long articles such as Sam splints and other elongated articles and materials and supplies as may be needed in tending battlefield injuries as first responder.

As shown best in FIG. 2, the chest bag of this invention includes means for supporting the second, lower section 10' in a substantially L-shape, tray-like open bag condition in which the lower section is held in a condition extending substantially perpendicularly from the first, upper section 10' at the fold hinge line 20. In the particular embodiment illustrated, this support means comprises a pair of elongated flexible cord members 50, each secured at their opposite terminal ends to the respective upper and lower bag sections 10', 10" adjacent the lateral sides of the sections.

As is apparent to those skilled in the art, the cord members may be provided, as shown herein, with an overall length sufficient to allow the front and rear bag panel members 10', 10" to pivot on hinge line 20 into the fully open bag condition of FIG. 3. In the embodiment illustrated, each said cord member includes a friction slide clamp fastener apparatus 52 arranged to releasably secure the respective cord member in a selected, reduced-length condition as in FIG. 2. These type of cord length-adjusting clamp fastener devices are well known, and need not be described in further detail herein.

Alternatively, it will also be apparent that the cord members 50 could if desired be provided in a fixed length selected to support and hold the lower section in the open, perpendicularly extending condition of FIG. 2, with one end of each cord member being releasably fastened to the associated upper or lower bag section. In this manner, when the cord members are connected at their opposite ends to the respective bag sections, the bag will open to and be supported in the condition of FIG. 2. However, by detaching the releasably-fastened ends of the cord members from their respective connections into one of the bag sections, the bag sections are freed to pivot on hinge line 20 into the fully open bag condition shown in FIG. 3.

Now with reference to the interior confines of the medical chest bag of this invention it will be seen that the interior wall panels 22, 24 mount a plurality of selected pockets and holders arranged to securely hold desired supplies in convenient manner for facilitated access when needed. In the particular embodiment illustrated, the interior panel 22 of the first upper section 10' of the chest bag mounts a pair of large pockets 54, each pocket being open at its upper end for securely holding IV bags and IV catheters.

Secured on the interior panel 22 between the large pockets 54 are a plurality of laterally-extending, vertically spaced-apart elastic straps 56 preferably arranged, as shown, in a molle-compatible configuration. These straps may be used to secure J-tubes, nasal airways, packs of petrolatum, adhesive tape and other supplies as may be needed or desired. Alternatively, these straps 56 can be used if desired as base securement straps to attach molle-compatible pocket members and other articles removably in the space between the pockets 54. The molle configuration is a well-known strap-type attachment system used by the military and therefore does not need to be further described in detail herein.

The interior wall panel 24 of the second, lower bag section 10" is illustrated herein as mounting three pocket members 58, each pocket preferably arranged to be releasably closable and accessible through both its opposite longitudinal ends. In this regard, each of the pocket members 58 seen herein includes an end closure flap member 60, 60' arranged to releasably overlie and close each corresponding open end of the pocket, whereby contents of the pocket are securely retained in the interior confines thereof. In the embodiment illustrated the flap members and pockets each mount one of corresponding fastener components (not shown) of a hook and loop type fastener arrangement, as is well known in the quick release fastener art.

This particular arrangement of pockets which are releasably openable on both opposite ends on the lower, hinged bag section 10" permits unhindered access to the interior confines of the pockets through their one ends associated with closure flap members 60' when the chest bag is disposed in its L-shaped, tray-like open condition of FIG. 2. In this open bag condition, access to the contents of the pockets 58 through their opposite ends associated with closure flap 60 is hindered by the closely adjacent, upstanding bag section 10'.

However, when the chest bag is in the second, fully open condition of FIG. 3, as when the chest bag is suspended in a hanging condition from a hook (not shown) by a hanger member 62 fixedly secured on the upper end of the rear exterior panel 26 on the first, upper bag section 10', the contents of the pockets 58 may tend to undesirably fall out of a pocket by gravity when a flap 60' is released to permit access to the interior confines of the pocket. Thus, since the upper section 10' is not in a hindering position when the bag is in its fully open condition of FIG. 3, the pockets may be most conveniently accessed by release of the overlying flap 60 as is readily apparent.

As seen best in FIGS. 1, 2 and 3, the chest bag of this invention is preferably also provided to be quickly closed and temporarily held in the closed condition of FIG. 1 when needed. In this regard the rear exterior panel 26 mounts one end portion of a closure flap member 64 arranged to overlie the confronting longitudinal edges 14, 16 of the chest bag when the bag is in its closed condition of FIG. 1 to releasably secure the bag in said closed condition. In this, the flap member 64 mounts one component 66 of a hook and loop type fastener, the corresponding component (not shown) of the hook and loop type fastener being secured on a confronting surface on the front exterior wall panel 28 of the bag. This arrangement permits the wearer to open the chest bag supported on his chest into the condition of FIG. 2 for access to and handling of medical supplies, while also allowing him to quickly close the bag temporarily in to the condition of FIG. 1 so that his view of and work on a patient is not hindered by the outwardly projecting, tray-like lower section 10" seen in FIG. 2.

Finally, as seen best in FIG. 1, the front exterior wall panel 28 of the chest bag is preferably provided with one or more external pockets 68 for carrying additional supplies, ammunition clips, grenades and other articles that may be needed or desired. As will be readily apparent, although such pockets may be permanently attached to the front wall of the bag if desired, they are preferably provided as separate, removable pocket members 68 and other articles which are releasably attached to the front wall panel by a selected quick release connection arrangement. In the particular embodiment illustrated in FIG. 1, pocket members 68 are secured to the chest bag by molle-configuration, strap-type attachment apparatus well known in and preferred by the military. These strap-type attachment arrangements provide a plurality of laterally extending, vertically spaced apart securement straps 70 on a base support panel such as the exterior front panel 28 of the chest bag of this invention. A corresponding set of laterally-extending, vertically-spaced apart securement straps (not shown) are provided on the confronting wall of a pocket member or other articles such as a holster to be secured onto the base support, for interwoven securement of the various laterally extending securement straps with one or more vertically oriented connector straps (not shown) secured on the pocket member or other article as is very well understood in the art.

From the foregoing it will be apparent to those skilled in the art that many various changes, other than those already discussed, may be made in the size, shape, type, number and arrangement of parts described hereinbefore without departing from the spirit of this invention and the scope of the appended claims.

Having thus described my invention and the manner in which it may be used, I claim:

1. A chest bag comprising:
   a chest bag body with a rear bag panel and an opposite front bag panel defining therebetween an interior of the chest bag body for carrying articles therein;

a shoulder harness connected to the rear bag panel, the shoulder harness wearable by a person for securing the chest bag body against the person's chest;

a fastener releasably attaching the front bag panel to the rear bag panel in a facing condition, the front bag panel attached to the rear bag panel along a bottom margin of the rear bag panel such that when the fastener is released the front bag panel is pivotally moveable outwardly from the rear bag panel to an open condition; and a flexible elongate panel support member secured at its opposite ends to the respective front and rear bag panels, wherein the opposite ends are fastened on the interior of the chest bag body, the panel support member supporting the front bag panel relative to the rear bag panel when the chest bag is open such that the front bag panel extends outwardly from the body of a person's chest in a tray-like configuration when the person is wearing the chest bag.

2. The chest bag of claim 1, wherein the flexible elongate panel support member is extendable to allow the chest bag to hang downwardly from the bottom margin of the rear bag panel.

3. The chest bag of claim 2, wherein the panel support member includes a length-adjusting fastener for extending the panel support member.

4. The chest bag of claim 1, wherein the panel support member comprises at least one cord.

5. The chest bag of claim 1, wherein the chest bag further comprises at least one storage pocket mounted on an interior side of the front bag panel, the storage pocket including releasable top and bottom closure flaps at opposing top and bottom ends of the storage pocket, respectively, for allowing access to articles contained in the storage pocket when the chest bag is in the open condition.

6. The chest bag of claim 1, wherein the chest bag further comprises at least one exterior storage pocket mounted on an exterior wall of the front bag panel.

7. The chest bag of claim 1, wherein the shoulder harness further comprises first and second shoulder straps connected to the chest bag body via corresponding first and second quick-release buckle connectors mounted on the rear bag panel member, the shoulder straps arranged to extend over the wearer's shoulders and downwardly along the wearer's back such that the straps cross and pass around the sides of the wearer's torso for connection to the rear bag panel member.

8. The chest bag of claim 7, wherein both ends of each of the first and second shoulder straps are detachably engaged to quick-release buckle connectors mounted on the rear bag panel to allow for complete separation of the chest bag from the shoulder harness and from the person when the quick-release buckles are released.

9. The chest bag of claim 1, further comprising a waist strap to releasably secure the chest bag body to the person.

10. The chest bag of claim 1, wherein the fastener comprises a slider-type fastener including interengaging fastener components extending around outer peripheral edges of the front and rear bag panel members.

11. The chest bag of claim 10, wherein the fastener comprises a zipper.

12. The chest bag of claim 1, further comprising a closure flap arranged to overlie confronting top edges of the front and rear bag panel members when in the closed position and to releasably secure the front bag panel member in the closed position via interengaging portions of hook-and-loop fastener material mounted on the respective closure flap and chest bag body.

13. The chest bag of claim 1, further comprising a hanger secured to an upper end of the rear bag panel.

14. A chest bag arranged to be worn and supported against the chest of a wearer in both a first, closed, carrying condition and in a second, open condition for access to the interior of the chest bag, the chest bag comprising:

a) a flexible chest bag body comprising a first, rear bag panel member and a second, opposite, front bag panel member, each of said bag panel members defining interior and exterior bag sides, wherein the interior bag sides face each other when the bag is in the closed condition top and bottom ends, and lateral side edges, said first and second bag panel members pivotally connected together along corresponding, confronting bottom ends for hinged, pivotal movement of the second, front bag panel member on the first, rear bag panel member, b) a fastener apparatus on the chest bag body at said lateral side edges and top ends of said first and second bag panel members the fastener apparatus having a fastened position that releasably secures the first and second bag panel members together in a closed bag condition and an unfastened position that releases the first and second panel members for pivotal movement of the front bag panel member into an open bag condition for access to the interior of the chest bag, and c) a flexible support fastened to said first bag panel member interior bag side and fastened to said second bag panel member interior bag side, wherein said flexible support releasably engages at least one of said first or second bag panel member interior sides, the support having a length to hold the second, front bag panel member in a substantially perpendicularly-extending, substantially L-shaped, tray-like open bag condition on the first, rear bag panel member when the chest bag is in an open condition and the support engages both the first and second bag panel members, and d) shoulder-encircling securement straps on the first, rear bag panel member arranged to position and secure the chest bag body to a wearer in position against the chest of the wearer for hands-free carrying of the chest bag and access to the interior of the chest bag worn by the wearer.

15. The chest bag of claim 14 wherein said flexible support further includes a length-adjusting fastener attached to the flexible support;

wherein the flexible support and the length-adjusting fastener have a first position that provides a first length for the flexible support to hold the second, front bag panel member in a substantially perpendicularly-extending, substantially L-shaped, tray-like open bag condition on the first, rear bag panel member when the chest bag is in an open condition and the flexible support engages both the first and second bag panel members; and wherein the flexible support and the length-adjusting fastener have a second position that provides a second length for the flexible support that is greater than the first length to hold the second, front bag panel member in a full open condition on the first, rear bag panel member with the flexible support engaging both the first and second bag panel members.

16. The chest bag of claim 15 wherein said flexible support includes at least one cord.

17. The chest bag of claim 14 wherein said flexible support includes at least one cord.

18. The chest bag of claim 14 wherein said fastener apparatus includes a slide fastener apparatus releasably interconnecting the lateral side edges and top end of said first and second bag panel members together.

19. The chest bag of claim 14 further comprising a waist-encircling securement strap adjacent the bottom of the first, rear bag panel member.

20. The chest bag of claim 14 wherein said shoulder-encircling straps are mounted on the first, rear bag panel member by quick release connectors arranged to permit quick disconnection of the shoulder straps and the chest bag for quick separation of the chest bag from the wearer when desired.

21. The chest bag of claim 14 including a plurality of individual storage pockets mounted on said exterior bag sides and arranged to contain selected supplies and materials for access when the chest bag is in closed condition supported on a wearer.

22. The chest bag of claim 14 including a plurality of individual storage pockets mounted on said interior bag sides and arranged to contain selected supplies and articles for access when the chest bag is in open condition.

23. The chest bag of claim 14, further comprising MOLLE-compatible straps attached to the chest bag body in spaced-apart configuration for attachment of articles to the chest bag.

* * * * *

UNITED STATES PATENT AND TRADEMARK OFFICE
CERTIFICATE OF CORRECTION

PATENT NO. : 7,712,645 B2  Page 1 of 1
APPLICATION NO. : 11/732532
DATED : May 11, 2010
INVENTOR(S) : Carston R. Calkin It is certified that error appears in the above-identified patent and that said Letters Patent is hereby corrected as shown below:

In column 1, line 7, replace "60/193,542" with --60/793,542--.

In column 7, line 12, replace "on" with --to--.

In column 8, line 11, replace "the bag is in the closed condition" with --the chest bag body is in a closed condition,--.

In column 8, line 25, delete the word "and".

Signed and Sealed this

Thirteenth Day of July, 2010

David J. Kappos
*Director of the United States Patent and Trademark Office*